United States Patent [19]

Fischer

[11] Plant 4,536

[45] May 20, 1980

[54] AFRICAN VIOLET CULTIVAR NAMED GRACE

[75] Inventor: Arnold W. Fischer, Hanover, Fed. Rep. of Germany

[73] Assignee: Pan-American Plant Company, West Chicago, Ill.

[21] Appl. No.: 15,310

[22] Filed: Feb. 26, 1979

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Charles W. Rummler

[57] ABSTRACT

A new African violet variety distinguished by its flowers of a distinct light blue color borne in clusters on sturdy main stems to the side and somewhat above dark green and shiny foliage, its vigorous, strong and rapid growth, and the pink under sides of its abundant oval leaves.

1 Drawing Figure

BACKGROUND OF THE NEW PLANT

My new African violet plant was discovered by me in 1972 growing as a seedling of unknown parentage in my greenhouse at Hanover, Germany, where I was seeking to develop improved varieties of violets for commercial exploitation. The attractive light blue color of the blossoms of this plant caused me to propagate it by leaf cuttings for test purposes; and subsequent reproduction by like means through successive generations at Hanover, Germany, and at West Chicago, Ill., U.S.A., has demonstrated that this plant retains its distinctive characteristics from generation to generation and has favorable advantages for the commercial market. Propagation for marketing purposes is now being done by means of vegetative cuttings at West Chicago, Ill., U.S.A.

DESCRIPTION OF THE DRAWING

My new African violet is illustrated by the accompanying full color photographic drawing which shows a potted plant in full bloom, the view showing the form and arrangement of the blossoms and the foliage, the colors shown being as nearly true as it is reasonably possible to obtain by professional photographic procedures.

DESCRIPTION OF THE NEW PLANT

The following is a detailed description of my new cultivar of African violet based upon observations of greenhouse grown plants at West Chicago, Ill., the color designations being according to The R.H.S. Colour Chart of The Royal Horticultural Society of London, England.

THE PLANT

Origin: Seedling.

Parentage: Unknown.

Classification: Botanic — Saintpaulia Ionantha. Commercial — African violet potted plant.

Form: Compact rosette.

Growth: Rapid, vigorous and strong.

Foliage: Abundant with about 20 leaves.

*Size of leaf.*—From very small to length of about 7.62 cm. and width of about 6.8 cm.

*Shape of leaf.*—Oval with rounded to an acute apex and with repand margin.

*Texture.*—Pubescent.

*Aspect.*—Glossy.

*Color.*—Upper side — 139A. Under side — 63B.

*Ribs and veins.*—Pinnate.

*Petioles.*—Length — about 1.27 cm. to about 5.71 cm.

THE BUD

Form: Vase shaped.

Size: Variable in diameter and length from flower to flower and plant to plant.

Opening rate: Average for typical African violets.

Color of petals: When sepals first divide — 155A. When petals begin to unfurl — 94A.

Sepals: 5 in number and branched.

*Shape.*—Lanceolate and becoming flat when flowers open.

*Color.*—Inside — 199A. Outside — 199A.

Calyx:

*Shape.*—Calyx splits to star shape.

*Size.*—Small.

*Aspect.*—Hairy.

Peduncle:

*Length.*—About 4.44 cm. to 6.03 cm.

*Strength.*—Erect and rigid.

*Aspect.*—Hairy.

*Color.*—199A.

THE FLOWER

Blooming habit: Continuous and profuse the year around.

Borne: In clusters as a cyme.

Size of flower: Medium. About 4 cm. in diameter and flat.

Shape: When bloom first opens — Cup-shaped becoming flat when the bloom matures.

Petalage:

*Number of petals.*—5, 3 of them larger than the other 2.

*Arrangement.*—Sympetalous.

*Form.*—Zygomorphic with rounded apex and repand margin.

*Texture.*—Glabrous.

*Appearance.*—Satiny.

*Color.*—Top side — 94B. Bottom side — 94D.

*Petaloids.*—Number — 2 to 4. Size: Insignificant and variable and clustered around stamens. Color: 94A to 96C.

Peduncle: Length — about 4.44 cm. to 6.03 cm.

*Color.*—199A.

*Strength.*—Upright and sturdy.

Persistence: Flowers hang on and dry.

Discoloration after full bloom: Color becomes a darker blue as it dries.

Fragrance: None

Lasting quality: 10 to 14 days.

REPRODUCTIVE ORGANS

Stamens:

*Number.*—Four.

*Arrangement.*—Monadelphous.

*Anthers.*—about 3.18 mm. in size and yellow in color.

*Filaments.*—Length — about 3.18 mm. Color: Violet.

*Pollen.*—Color — Yellow.

Pistils: Number — One.

*Style.*—About 9.52 mm. in length. Color: Violet.

*Stigma.*—Color — White.

Ovaries: Hypogynous and tomentose.

This new African violet cultivar is particularly characterized by its dark green and shiny foliage which has a distinctive pink under side. The flower form is a typical violet, zygomorphic with a sympetalous and rotate corolla with three large and two small petals and two to four petaloids clustered around the stamens. The color is a distinct light blue and the flowers are borne in clusters on sturdy peduncles somewhat above the dark green foliage. Flowering of this new variety is continuous under optimal conditions.

I claim:

1. A new and distinct African violet, substantially as herein shown and described, characterized by its distinct light blue flowers borne in clusters on sturdy stems to the side and somewhat above dark shiny green foliage which, in turn, is characterized by pink under sides.

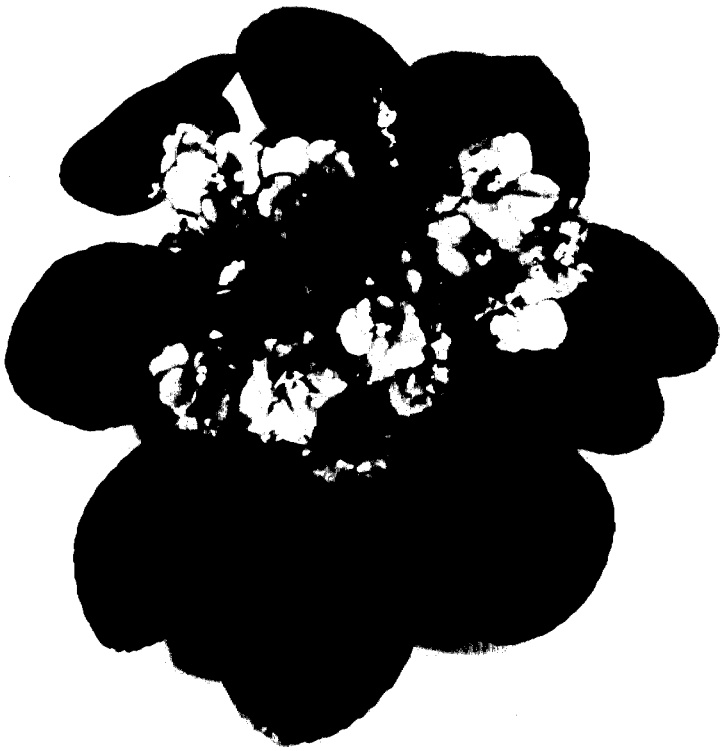

* * * * *